US012576163B2

(12) United States Patent
Wang et al.

(10) Patent No.: US 12,576,163 B2
(45) Date of Patent: Mar. 17, 2026

(54) FLUORESCENT CONTRAST AGENT WITH TARGETING FUNCTION, AND PREPARATION METHOD AND USE THEREOF

(71) Applicants: Peking University Third Hospital, Beijing (CN); Ordos Clinical Medical College of Inner Mongolia Medical University, Ordos City (CN)

(72) Inventors: Shumin Wang, Beijing (CN); Xiaolong Liang, Beijing (CN); Duo Zhao, Beijing (CN); Shiyuan Yang, Beijing (CN); Menghong Xu, Beijing (CN); Huiwen Li, Beijing (CN)

(73) Assignees: Peking University Third Hospital, Beijing (CN); Ordos Clinical Medical College of Inner Mongolia. Medical University, Ordos City (CN)

( * ) Notice: Subject to any disclaimer, the term of this patent is extended or adjusted under 35 U.S.C. 154(b) by 993 days.

(21) Appl. No.: 17/661,305

(22) Filed: Apr. 29, 2022

(65) Prior Publication Data

US 2023/0346982 A1     Nov. 2, 2023

(51) Int. Cl.
*A61K 49/00*          (2006.01)

(52) U.S. Cl.
CPC ...... *A61K 49/0002* (2013.01); *A61K 49/0052* (2013.01)

(58) Field of Classification Search
CPC ............ A61K 49/0002; A61K 49/0052; A61K 49/0021; A61K 49/0043; A61K 49/0082
See application file for complete search history.

(56) References Cited

U.S. PATENT DOCUMENTS

2021/0196832 A1* 7/2021 Song .................. A61K 47/6907
2025/0049963 A1* 2/2025 Rangaramanujam .......................
                                                   A61K 49/0054

OTHER PUBLICATIONS

Chen et al., Theranostic 2019, vol. 9, Issue 1 (Year: 2019).*

* cited by examiner

*Primary Examiner* — Robert S Cabral
(74) *Attorney, Agent, or Firm* — Hoffman Warnick LLC

(57) ABSTRACT

The present disclosure provides a fluorescent contrast agent with a targeting function, and a preparation method and a use thereof, and belongs to the technical fields of nanomaterials and biomedical materials. The fluorescent contrast agent (MR780 NPs) of the present disclosure can specifically bind to CD206 on a surface of tumor-associated macrophages (TAMs). MR780 NPs accumulate in lymph nodes invaded by tumor cells and undergo an oxidation-reduction reaction with reduced glutathione in a tumor microenvironment, which triggers a fluorescence signal of MR780 NPs; and MR780 NPs do not accumulate and do not show fluorescence in normal lymph nodes. Therefore, the fluorescent contrast agent of the present disclosure can be used to diagnose lymph node metastasis (LNM) of breast cancer, realize the preoperative evaluation of LNM, assist in the clinical determination of tumor staging and the formulation of a surgical plan, and achieve the accurate resection under intraoperative fluorescence navigation.

17 Claims, 14 Drawing Sheets

Cell morphology after 24 h of
induction with RAW264.7 + IL4

FIG. 11A
FIG. 11B
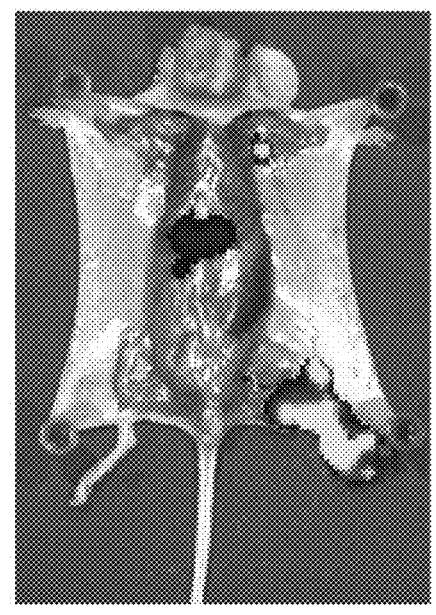
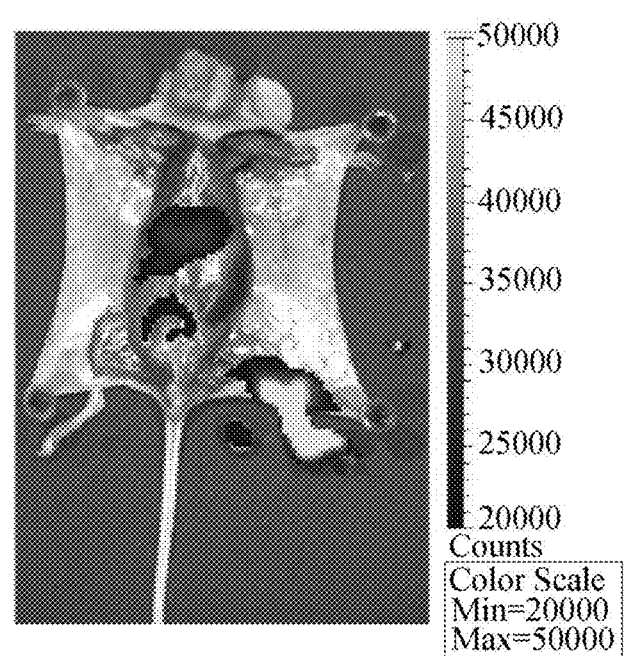
FIG. 11C
Normal group
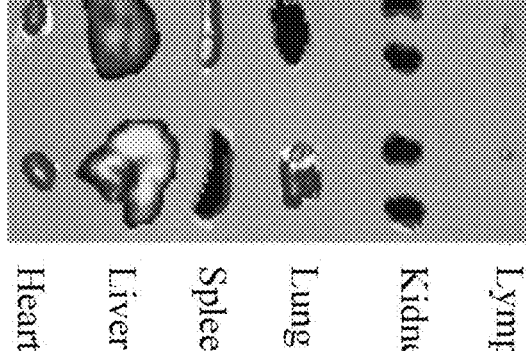
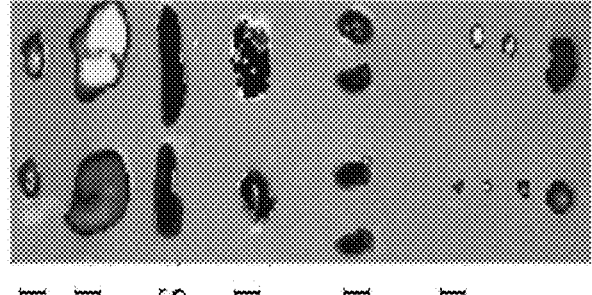

FIG. 12
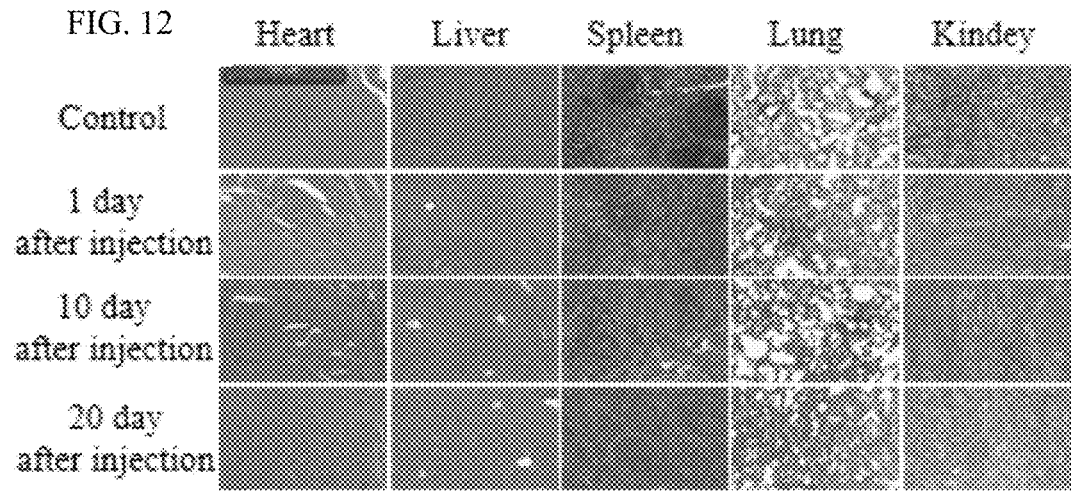
FIG. 13A                                    FIG. 13B
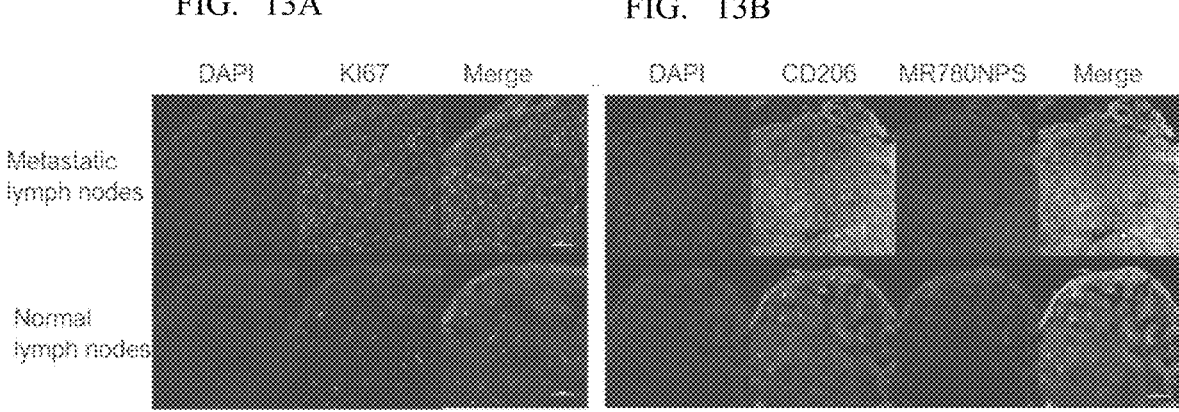

FLUORESCENT CONTRAST AGENT WITH TARGETING FUNCTION, AND PREPARATION METHOD AND USE THEREOF

TECHNICAL FIELD

The present disclosure relates to the technical fields of nanomaterials and biomedical materials, and in particular to a fluorescent contrast agent with a targeting function, and a preparation method and a use thereof.

BACKGROUND ART

Whether there is axillary lymph node metastasis (ALNM) is an important factor affecting the prognosis of early breast cancer (EBC). Ultrasound is the main method of breast cancer screening, through which the condition of lymph nodes can be preliminarily determined. In contrast-enhanced ultrasound (CEUS), the internal contrast agent perfusion needs to be observed for locally-infiltrated lymph nodes, where the contrast agent can be fully visualized in a normal part of the lymph nodes and the contrast agent presents a filling defect in a part of the lymph nodes occupied by tumor cells. Due to contrast agent spillage, it is impossible to determine whether lymph nodes are occupied by tumor cells in an early stage of metastasis; and because the entire lymphatic channel is filled with tumor thrombi in a late stage of metastasis, a contrast agent cannot pass smoothly, which may cause the overall failed visualization and thus lead to missed diagnosis. Magnetic resonance imaging (MRI) is now more and more widely used in the diagnosis of lymph node metastasis (LNM) of breast cancer. However, the partial volume effect (PVE) tends to occur due to the small size of lymph nodes, a spatial resolution of MRI cannot clearly distinguish the structures of the lymph node cortex and medulla, and sometimes MRI is affected by artifacts generated due to cardiac impulse, which makes MRI limited in the diagnosis of LNM. The imaging diagnosis of benign and malignant lymph nodes in breast cancer patients is currently a challenging clinical problem.

As the most potential targeting group, the mannose group has many advantages such as non-toxicity, non-immunogenicity, prominent biocompatibility, and excellent biodegradability. However, mannose is a simple natural ligand and is easily metabolized and cleared rapidly as a small molecular substance, and thus cannot be used as a prominent targeting agent. Therefore, how to design a fluorescent contrast agent with a mannose group as a targeting group for imaging diagnosis of benign and malignant lymph nodes in breast cancer patients is the key to the research.

SUMMARY

The present disclosure is intended to provide a fluorescent contrast agent with a targeting function, and a preparation method and a use thereof. The fluorescent contrast agent can improve the local retention effect to achieve long-term accurate targeting of M2 tumor-associated macrophages (TAMs) and non-invasive imaging (two major breakthroughs), and shows high specificity and sensitivity in the diagnosis of metastatic lymph nodes.

To achieve the objective of the present disclosure, the present disclosure provides the following technical solutions.

The present disclosure provides a fluorescent contrast agent with a targeting function, where the fluorescent contrast agent includes a targeting material, a fluorescent probe, and a nanoformulation material; and in the fluorescent contrast agent, the nanoformulation material serves as a carrier, and the targeting material and the fluorescent probe are linked through a disulfide bond molecule.

Preferably, the fluorescent contrast agent may have a particle size of 65 nm to 80 nm.

Preferably, the targeting material may be mannose and/or a mannose derivative.

Preferably, the fluorescent probe may be IR780, Cy5.5, IR820, Cy7, or Cy7.5.

Preferably, a disulfide bond molecule-containing compound may include one selected from the group consisting of cystamine, 3-[(3-amino-3-oxopropyl)dithio]propanamide, and D-cystine.

Preferably, the nanoformulation material may be PEGylated phospholipid.

Preferably, the mannose derivative may include 4-aminophenyl-α-D-mannopyranoside or D-mannosamine hydrochloride.

Preferably, the PEGylated phospholipid may include DSPE-PEG2000, DSPE-PEG5000, DPPE-PEG2000, DPPE-PEG5000, DMPE-PEG2000, or DMPE-PEG5000.

The present disclosure also provides a preparation method of the fluorescent contrast agent, including the following steps:

subjecting mannose or a mannose derivative to a carboxylation reaction with succinic anhydride to obtain carboxylated mannose or a carboxylated mannose derivative;

subjecting the fluorescent probe to an amination reaction with a disulfide bond molecule-containing compound to obtain an amino-modified fluorescent probe;

activating the carboxylated mannose or carboxylated mannose derivative, and subjecting the activated carboxylated mannose or carboxylated mannose derivative to a condensation reaction with the amino-modified fluorescent probe to obtain a mannose/mannose derivative-fluorescent probe conjugate; and subjecting the mannose/mannose derivative-fluorescent probe conjugate, PEGylated phospholipid, and water to ultrasonic dispersion to obtain the fluorescent contrast agent.

Preferably, the carboxylated mannose or carboxylated mannose derivative may be activated with a 1-ethyl-3-(3-dimethylaminopropyl)carbodiimide salt.

Preferably, a molar ratio of the carboxylated mannose or carboxylated mannose derivative to the succinic anhydride may be 1:(2-10).

Preferably, a molar ratio of the carboxylated mannose or carboxylated mannose derivative to the amino-modified fluorescent probe may be (1-10):1.

Preferably, the ultrasonic dispersion may be conducted for 5 min to 30 min with an ultrasonic temperature of 20° C. to 60° C. and an ultrasonic power of 50 W to 500 w.

Preferably, the carboxylation reaction and the amination reaction may be each conducted in an organic solvent.

Preferably, the amination reaction between the fluorescent probe and the disulfide bond molecule-containing compound may be conducted in the presence of a catalyst.

Preferably, the organic solvent may include N,N-dimethylformamide (DMF), N,N-dimethylacetamide (DMA), or dimethyl sulfoxide (DMSO).

Preferably, the catalyst may include 2,6-diisopropylaniline (DIPA), triethylamine (TEA), pyridine, N,N-diisopropylethylamine (DIPEA), or 4-dimethylaminopyridine (DMAP).

Preferably, the fluorescent probe, the disulfide bond molecule-containing compound, and the catalyst may be in a molar ratio of 1:(5-15):(10-30).

The present disclosure also provides a use of the fluorescent contrast agent described above, including any one selected from the group consisting of the following:

(1) a use of the fluorescent contrast agent for targeting M2 TAMs; and (2) a use of the fluorescent contrast agent in the diagnosis of metastatic lymph nodes.

Compared with the prior art, the present disclosure has the following beneficial effects:

(1) The present disclosure provides a fluorescent contrast agent with a targeting function. The fluorescent contrast agent can improve the local retention effect to achieve long-term accurate targeting of TAMs and non-invasive imaging (two major breakthroughs), and shows high specificity and sensitivity in the diagnosis of metastatic lymph nodes.

(2) The present disclosure also provides a preparation method and a use of the fluorescent contrast agent. In the preparation method, the near-infrared (NIR) dye IR780 is combined with 4-aminophenyl-α-D-mannopyranoside, and self-assembly is conducted through DSPE-PEG2000 to obtain the fluorescent contrast agent (MR780NPs), which improves the local retention effect to achieve the two major breakthroughs of long-term accurate targeting and non-invasive imaging. The MR780NPs of the present disclosure can tightly bind to CD206 on a surface of M2 TAMs through a specific ligand-receptor interaction to achieve high M2/M1 selectivity, and utilizes a nanoformulation to maximize the internalization of TAMs for MR780NPs. In addition, a fluorescence signal of MR780NPs is pre-blocked by a disulfide bond during the synthesis process. When enriched in metastatic lymph nodes, MR780NPs undergo an oxidation-reduction reaction with high-concentration reduced glutathione in a tumor microenvironment, such that the disulfide bond is broken and nanoparticles disintegrate to enable MR780NPs to emit tumor microenvironment-responsive fluorescence, thereby identifying metastatic lymph nodes. Reduced glutathione is expressed in large amounts in the tumor microenvironment to support the survival and proliferation of tumor cells, promote the tumor growth, and resist chemotherapeutic drugs. However, a reduced glutathione level is extremely low in normal or inflammatory lymph nodes, and MR780NPs cannot emit fluorescence in this environment. The present disclosure utilizes this characteristic as a fluorescence switch to differentiate between metastatic and non-metastatic lymph nodes. In addition, the preparation method of the present disclosure is simple and fast.

BRIEF DESCRIPTION OF THE DRAWINGS

FIG. 7 shows the specific uptake of M2 macrophages for FITC-MR780 NPs, where

FIG. 10 shows the fluorescence imaging and ultrasound imaging of metastatic lymph nodes in plantar 4T1 tumor models, where

FIG. 11 shows the resection of metastatic lymph nodes under fluorescence navigation, where FIG. 11A shows the fluorescence imaging of metastatic lymph nodes in tumor-bearing mice with skin removal at 24 h of peritumoral injection of MR780 NPs; FIG. 11B shows the resection of metastatic lymph nodes under fluorescence navigation; and FIG. 11C shows the fluorescence imaging of isolated mouse tissues and organs;

FIG. 12 shows the H&E staining of important tissues after injection of MR780 NPs (scale bar: 500 μm);

FIG. 13A shows the immunofluorescence staining of KI67 in metastatic lymph nodes and FIG. 13B shows the expression of CD206 in metastatic lymph nodes and the aggregation and co-localization of MR780 NPs in metastatic lymph nodes (scale bar: 100 μm)

DETAILED DESCRIPTION OF THE EMBODIMENTS

Figure 1:
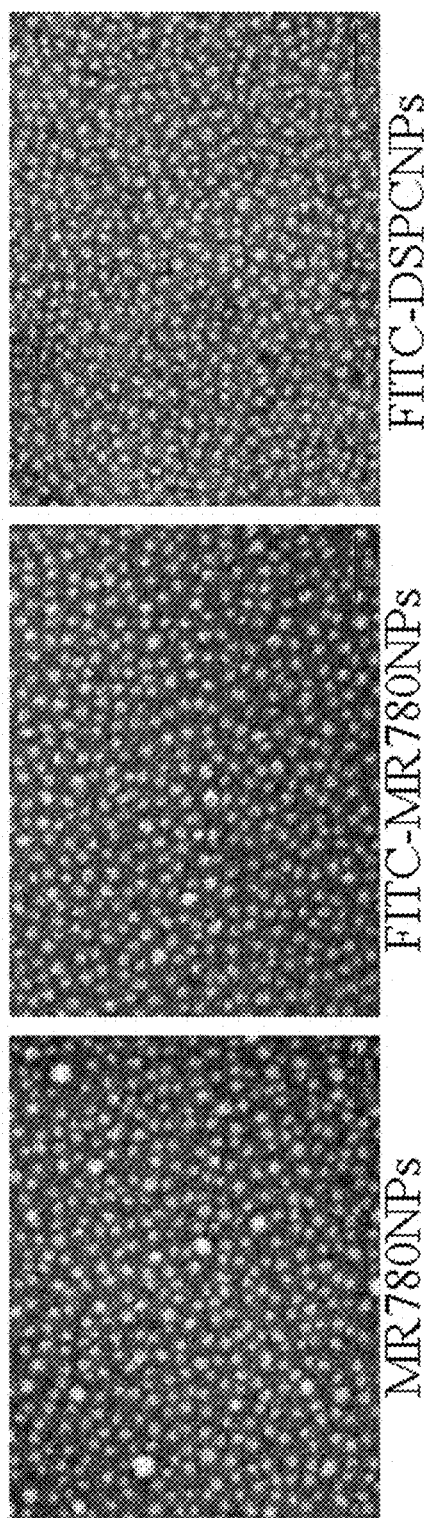
FIG. 1 shows the morphology (scale bar=50 nm) of MR780 NPs, FITC-MR780 NPs, and FITC-DSPC NPs observed by a transmission electron microscope.

The present disclosure provides a fluorescent contrast agent with a targeting function, where the fluorescent contrast agent includes a targeting material, a fluorescent probe, and a nanoformulation material; and in the fluorescent contrast agent, the nanoformulation material serves as a carrier, and the targeting material and the fluorescent probe are linked through a disulfide bond molecule.

In the present disclosure, the fluorescent contrast agent can tightly bind to CD206 on a surface of M2 TAMs through a specific ligand-receptor interaction to achieve high M2/M1 selectivity; and the targeting material may preferably be mannose and/or a mannose derivative, and further, the mannose derivative may include 4-aminophenyl-α-D-mannopyranoside or D-mannosamine hydrochloride. In the present disclosure, the fluorescent probe may preferably be IR780, Cy5.5, IR820, Cy7, or Cy7.5. The nanoformulation material may preferably be PEGylated phospholipid, and further, the PEGylated phospholipid may preferably include DSPE-PEG2000, DSPE-PEG5000, DPPE-PEG2000, DPPE-PEG5000, DMPE-PEG2000, or DMPE-PEG5000. In the present disclosure, the nanoformulation is used to maximize the internalization of TAMs for MR780NPs, making MR780NPs stable. In the present disclosure, a signal of the fluorescent dye IR780 is pre-blocked by a disulfide bond. When enriched in metastatic lymph nodes, MR780NPs undergo an oxidation-reduction reaction with high-concentration reduced glutathione in a tumor microenvironment, such that the disulfide bond is broken and nanoparticles disintegrate to enable MR780NPs to emit tumor microenvironment-responsive fluorescence, thereby identifying metastatic lymph nodes. The disulfide bond molecule-containing compound may preferably include one selected from the group consisting of cystamine, 3-[(3-amino-3-oxopropyl)dithio]propanamide, and D-cystine.

The present disclosure also provides a preparation method of the fluorescent contrast agent, including the following steps:

subjecting mannose or a mannose derivative to a carboxylation reaction with succinic anhydride to obtain carboxylated mannose or a carboxylated mannose derivative;

subjecting the fluorescent probe to an amination reaction with a disulfide bond molecule-containing compound to obtain an amino-modified fluorescent probe;

activating the carboxylated mannose or carboxylated mannose derivative, and subjecting the activated carboxylated mannose or carboxylated mannose derivative to a condensation reaction with the amino-modified fluorescent probe to obtain a mannose/mannose derivative-fluorescent probe conjugate; and subjecting the mannose/mannose derivative-fluorescent probe conjugate, PEGylated phospholipid, and water to ultrasonic dispersion to obtain the fluorescent contrast agent.

As a preferred embodiment, the present disclosure also provides a preparation method of the fluorescent contrast agent, including the following steps:

subjecting 4-aminophenyl-α-D-mannopyranoside to a carboxylation reaction with succinic anhydride to obtain a carboxylated 4-aminophenyl-α-D-mannopyranoside compound;

subjecting the fluorescent probe IR780 to an amination reaction with cystamine dihydrochloride to obtain an amino-modified fluorescent probe;

activating the carboxylated 4-aminophenyl-α-D-mannopyranoside compound, and subjecting the activated carboxylated 4-aminophenyl-α-D-mannopyranoside compound to a condensation reaction with the amino-modified fluorescent probe to obtain a mannose-IR780 conjugate, namely, MR780; and subjecting the MR780, DSPE-PEG2000, and water to ultrasonic dispersion to obtain the fluorescent contrast agent.

In the present disclosure, mannose or a mannose derivative is subjected to a carboxylation reaction with succinic anhydride to obtain carboxylated mannose or a carboxylated mannose derivative. As a preferred embodiment, the carboxylation reaction may be conducted in an organic solvent, and the organic solvent may preferably include DMF, DMA, or DMSO. A molar ratio of the carboxylated mannose or carboxylated mannose derivative to the succinic anhydride may be 1:(2-10).

In the present disclosure, the fluorescent probe is subjected to an amination reaction with a disulfide bond molecule-containing compound to obtain an amino-modified fluorescent probe. As a preferred embodiment, the amination reaction between the fluorescent probe and the disulfide bond molecule-containing compound may be conducted in the presence of a catalyst. The catalyst may preferably include DIPA, TEA, pyridine, DIPEA, or DMAP. The amination reaction may be conducted in an organic solvent, and the organic solvent may preferably include DMF, DMA, or DMSO. The fluorescent probe, the disulfide bond molecule-containing compound, and the catalyst may preferably be in a molar ratio of 1:(5-15):(10-30).

In the present disclosure, the carboxylated mannose or carboxylated mannose derivative is activated and then subjected to a condensation reaction with the amino-modified fluorescent probe to obtain a mannose/mannose derivative-fluorescent probe conjugate. As a preferred embodiment, the carboxylated mannose or carboxylated mannose derivative may be activated with a 1-ethyl-3-(3-dimethylaminopropyl) carbodiimide salt. A molar ratio of the carboxylated mannose or carboxylated mannose derivative to the amino-modified fluorescent probe may be preferably (1-10):1 and more preferably (2-5):1.

In the present disclosure, the mannose/mannose derivative-fluorescent probe conjugate, PEGylated phospholipid, and water are subjected to ultrasonic dispersion to obtain the fluorescent contrast agent. The ultrasonic dispersion may be conducted for preferably 5 min to 30 min and more preferably 10 min to 20 min; the ultrasonic dispersion may be conducted with an ultrasonic temperature of preferably 20° C. to 60° C. and more preferably 40° C. to 50° C.; and the ultrasonic dispersion may be conducted with an ultrasonic power of preferably 50 W to 500 w and more preferably 100 W to 300 W. The fluorescent contrast agent of the present disclosure may have a particle size of preferably 65 nm to 80 nm. In the present disclosure, the fluorescent contrast agent is a nano-scale contrast agent, which can smoothly pass through lymphatic vessels due to small particle size, such that TAMs can internalize MR780NPs to the maximum extent.

The present disclosure also provides a use of the fluorescent contrast agent described above, including any one selected from the group consisting of the following:

(1) a use of the fluorescent contrast agent for targeting M2 TAMs; and (2) a use of the fluorescent contrast agent in the diagnosis of metastatic lymph nodes.

In the present disclosure, unless otherwise specified, all raw material components are commercially available products well known to those skilled in the art.

The technical solutions of the present disclosure will be clearly and completely described below with reference to the examples of the present disclosure. Apparently, the described examples are merely some rather than all of the examples of the present disclosure. All other examples obtained by a person of ordinary skill in the art based on the examples of the present disclosure without creative efforts shall fall within the protection scope of the present disclosure.

In the examples, the 4-aminophenyl-α-D-mannopyranoside is purchased from Wuhan Kainuo Pharmaceutical Technology Co., Ltd. The IR780 is purchased from Aladdin Biochemical Technology Co., Ltd. The DSPE-FITC is purchased from Beijing J&K Scientific Ltd. The healthy BALB/c nude mice (6 weeks old, female, SPF grade) are purchased from Beijing Vital River Laboratory Animal Technology Co., Ltd.

In the examples, statistical analysis: the SPSS 22.0 statistical software is used for data processing, measurement data are expressed as mean±standard deviation, t-test is conducted for comparison among groups, and $P < 0.05$ indicates that there is statistical significance.

Example 1

1.1 A Preparation Method of a Fluorescent Contrast Agent, Including the Following Steps:

(1) In DMF, 4-aminophenyl-α-D-mannopyranoside and succinic anhydride were mixed in a molar ratio of 1:2 to allow a reaction for 24 h, then the DMF was evaporated by a rotary evaporator, 20 mL of dichloromethane (DCM) was added, unreacted succinic anhydride was filtered out, and methanol was added to a resulting supernatant to obtain a precipitate, which was a carboxylated 4-aminophenyl-α-D-mannopyranoside compound.

(2) The fluorescent probe IR780, cystamine dihydrochloride, and DIPA were mixed in a molar ratio of 1:5:10 in 4 mL of DMF, a resulting mixture was stirred overnight at room temperature, then DMF was evaporated by a rotary evaporator, and a resulting product was dissolved with DCM, washed 3 times with saturated sodium chloride, and dried overnight with anhydrous sodium sulfate to obtain an amino-modified fluorescent probe.

(3) 2 mol of the carboxylated 4-aminophenyl-α-D-mannopyranoside compound was activated with 4 mol of 1-ethyl-3-(3-dimethylaminopropyl)carbodiimide hydrochloride, then 1 mol of the amino-modified fluorescent probe was added at room temperature, a resulting mixture was stirred overnight, and then methanol was added and evaporated with a rotary evaporator to obtain a mannose derivative-IR780 conjugate (MR780).

(4) MR780 and DSPE-PEG2000 (2 mg in total) were mixed in a molar ratio of 95:5 in ethanol, a resulting mixture was subjected to an ultrasonic treatment for 15 min in a 40° C. water batch at 300 W and then uniformly dispersed in 1 mL of deionized water, and a resulting dispersion was subjected to dialysis in a dialysis bag (molecular weight cut-off (MWCO): 8,000 da to 14,000 da) for removing the organic solvent to obtain the fluorescent contrast agent (MR780 NPs).

FITC-DSPC NPs (an MR780-free fluorescent contrast agent) were prepared with DSPC, DSPE-PEG2000, and DSPE-FITC (in a molar ratio of 95:4.5:0.5).

FITC-MR780 NPs were prepared by a same method with MR780 NPs, DSPE-PEG2000, and DSPE-FITC (in a molar ratio of 95:4.5:0.5).

1.2 Characterization of MR780 NPs

A size of the contrast agent was detected with the Zetasizer nano-ZS. 10 μL of each of MR780 NPs, FITC-MR780

NPs, and FITC-DSPC NPs was taken and added dropwise on a mesh, air-dried, stained with phosphotungstic acid (10 μL, 3.0%), then washed with deionized water, and air-dried. Morphological images of the mannose contrast agents were acquired through high-resolution transmission electron microscopy (HRTEM). Since MR780 NPs need to emit reduced glutathione-responsive fluorescence in a tumor microenvironment, it must be ensured that MR780 NPs can stably restore the fluorescence signal after reacting with reduced glutathione. 10 μL of MR780 NPs was thoroughly mixed with 10 mM reduced glutathione, and a resulting mixture was shaken at room temperature in the dark; and the fluorescence restoration of MR780 NPs in each group was tested at 10 min, 1 h, 2 h, and 4 h. The UV-VIS spectroscopy and fluorescence spectroscopy were conducted respectively on a UV-VIS spectrophotometer and a fluorescence spectrophotometer.

It can be seen from FIG. 1 that the MR780 NPs, FITC-MR780 NPs, and FITC-DSPC NPs each are spherical under a transmission electron microscope, and have a relatively-dense size distribution in a PBS solution, without obvious aggregation.

Figure 2:
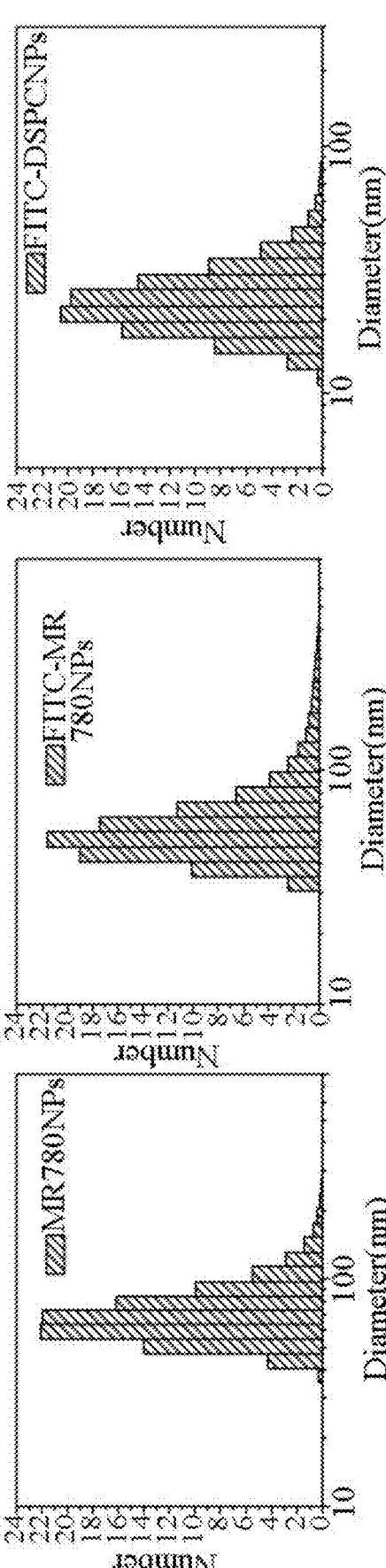
FIG. 2 shows the size distribution of MR780 NPs, FITC-MR780 NPs, and FITC-DSPC NPs in DLS.

It can be seen from FIG. 2 that, according to dynamic light scattering (DLS) tests, MR780 NPs have an average particle size of 72.81±4.39 nm, the FITC-MR780 NPs have an average particle size of 62.43±8.46 nm, and the FITC-DSPC NPs have an average particle size of 24.66±3.59 nm.

In conclusion, MR780NPs are uniformly dispersed in a physiological environment, with a particle size distribution of 72.81±4.39 nm, which is favorable for massive penetration into solid tumors and metastatic lymph nodes.

Figure 3A:
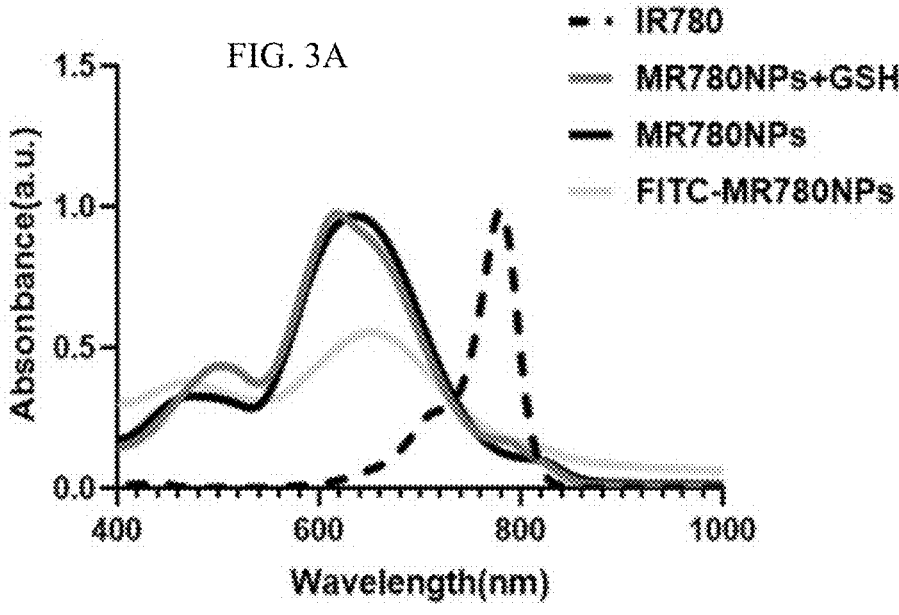
FIG. 3A shows the UV-VIS absorption spectra of IR780, MR780 NPs, MR780 NPs+10 mM GSH, and FITC-MR780 NPs.
Figure 3B:
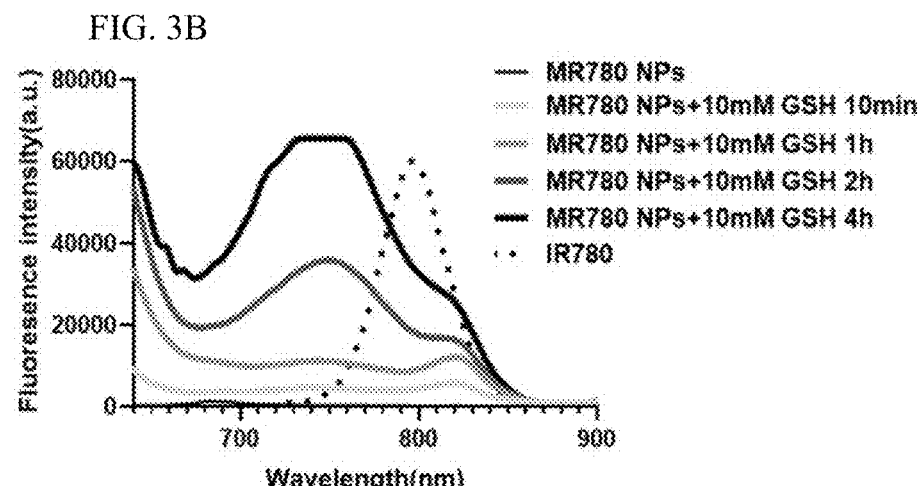
FIG. 3B shows the fluorescence spectra of MR780 NPs+10 mM GSH at different time points and the fluorescence spectrum of IR780.
Figure 3C:
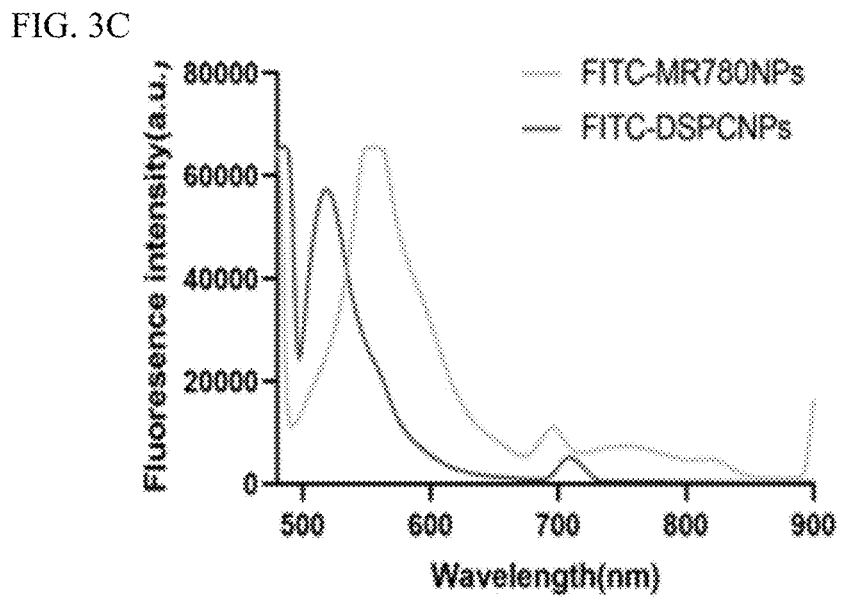
FIG. 3C shows the fluorescence spectra of FITC-MR780 NPs and FITC-DSPC NPs.

It can be seen from FIG. 3 that the UV-VIS spectrum of IR780 shows a maximum absorbance at 780 nm, and the UV-VIS spectrum of MR780 NPs shows a maximum absorption peak at 637 nm; after 10 mM reduced glutathione is added to the MR780 NP solution, the waveform does not change significantly (as shown in A of FIG. 3); the fluorescence spectrum shows that MR780 NPs have no obvious emission spectrum; and after 10 mM reduced glutathione is added to MR780 NPs, the fluorescence intensity is gradually restored with the reaction time, and the emission peak moves forward (as shown in B of FIG. 3). The fluorescence emission of FITC-DSPC NPs and FITC-MR780 NPs was detected, and a peak appeared at 525 nm to 575 nm (C in FIG. 3).

The UV-VIS spectroscopy shows that the change in the structural formula of IR780 during the synthesis process results in different UV absorptions of MR780 NPs and IR780, which requires excitation with 640 nm laser in animal experiments. After 10 mM reduced glutathione is added to the MR780 NP solution, the absorption spectrum shifts slightly forward, but the spectral morphology does not change. Since there is a large amount of reduced glutathione in a tumor microenvironment, MR780 NPs can be normally excited in this environment. The fluorescence spectrum of MR780 NPs shows no characteristic wave of IR780 at all, indicating the phenomenon of fluorescence blocking. After 10 mM reduced glutathione is added to MR780 NPs, the fluorescence intensity is gradually restored with the reaction time. In this case, the fluorescent contrast agent of the present disclosure undergoes an oxidation-reduction reaction, such that the disulfide bond of MR780 NPs is broken and the fluorescence signal is restored, thereby distinguishing metastatic lymph nodes from non-metastatic lymph nodes.

1.3 Cell Experiment

4T1-FLUC cells, a luciferase-transfected human breast cancer cell line, were purchased from the Institute of Basic Medicine, Chinese Academy of Medical Sciences, and were cultivated in a basal medium 1640 supplemented with 10% fetal bovine serum (FBS), 100 u/mL penicillin, and 100 mg/mL streptomycin. RAW264.7 cells, mouse mononuclear macrophage leukemia cells, were purchased from the Institute of Basic Medicine, Chinese Academy of Medical Sciences, and were cultivated in a DMEM supplemented with 10% FBS, 100 u/mL penicillin, and 100 mg/mL streptomycin. The cells were cultivated at 37° C. and 5% $CO_2$.

1.3.1 Nanoparticle Toxicity and Hemolysis Tests

The 3-(4,5-dimethylthiazol-2-yl)-2,5-diphenyltetrazolium bromide method (MTT) was used to evaluate the toxicity of nanoparticles. 4T1, RAW264.7, and HUVEC cells were cultivated at 37° C. and 5% $CO_2$. The cells were subcultivated, digested, and centrifuged to prepare a single-cell suspension with 5,000 cells/100 μL. A 96-well plate was opened, a row was adopted as an experimental group, and MR780 NP solutions were each added, with gradient concentrations of 0, 50, 100, 150, 200, and 250 (g/mL) from top to bottom. 24 h later, a solution in each well was taken out without touching a bottom, 100 μL of a medium was added, then 20 L of a methyl thiazolyl tetrazolium (MTT) solution (5 mg/mL) was added to each well, and the plate was incubated for 4 h. Then a solution in each well was removed, 150 μL of DMSO was added, a resulting mixture was shaken at room temperature for 10 min in the dark, and then the absorbance was determined at 490 nm on a microplate reader.

6-week-old female Balb/c nude mice each with a body weight of about 20 g were taken. Approximately 1 mL of fresh blood was collected from the heart with a 1 mL sterile syringe, and red blood cells (RBCs) were isolated from the plasma, centrifuged at 1,500 rpm/min for 15 min, washed 4 times with sterile PBS, and then diluted with 2 mL of PBS to obtain an RBC suspension. 1.0 mL of a PBS solution with pH 7.4 was adopted in a negative control group; 1.0 mL of an MR780 NP solution were adopted in each experimental group, with gradient MR780 NP concentrations of 0 μg/mL, 10 μg/mL, 20 μg/mL, 50 μg/mL, and 100 μg/mL; and 1.0 mL of deionized water was adopted in a positive control group. 1 mL of a sample was added to an EP tube, then 200 μL of the RBC suspension was added, and a resulting mixture was incubated in a constant temperature shaker for 2 h and then centrifuged at 1,500 rpm for 15 min; and 100 μL of a supernatant in each group was added to a 96-well plate, and the absorbance of the supernatant at a hemoglobin release wavelength of 576 nm was determined on a microplate reader.

Figure 4:
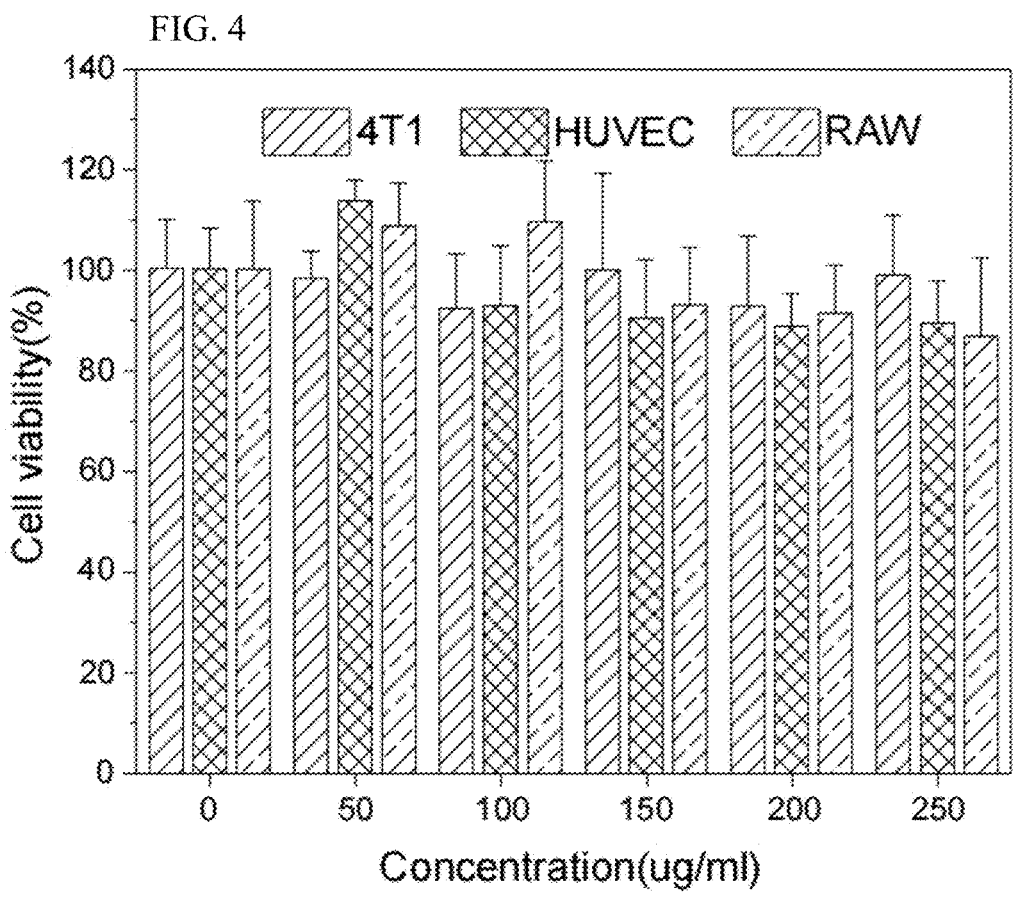
FIG. 4 shows the cell viabilities of 4T1, HUVEC, and RAW264.7 detected by MTT assay.

The MTT method was used to evaluate the differences in the toxicity of RAW264.7, HUVEC, and 4T1 cells in MR780 NP media at different concentrations. The results in FIG. 4 show that a cell survival rate in each group is >80%; there is no statistically significant difference among the groups (P>0.05); and MR780 NPs have high safety. Therefore, the cell experiment proves that MR780 NPs have little cytotoxicity and are safe and reliable.

Figure 5:
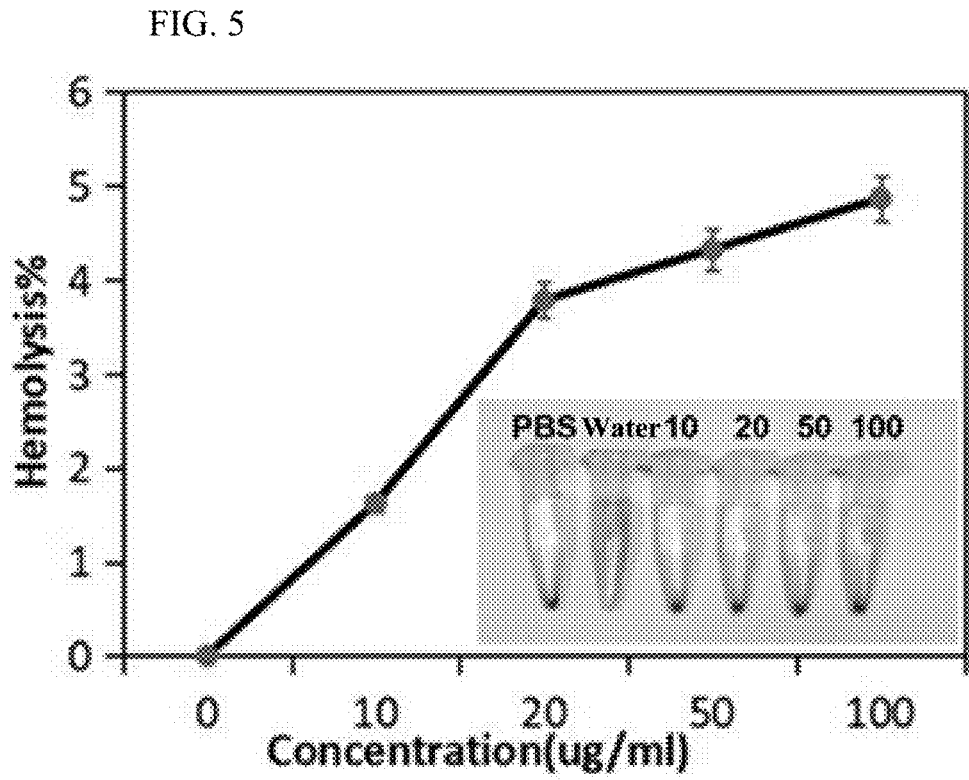
FIG. 5 shows the hemolysis rates of MR780 NPs at different concentrations (0 μg/mL, g/mL, 20 μg/mL, 50 μg/mL, and 100 μg/mL)

It can be seen from FIG. 5 that, in the hemolysis test, the MR780 NPs show prominent biocompatibility and have almost no destructive effect on RBCs; and the hemolysis rate of MR780 NPs increases slightly with the increase of concentration, but the hemolysis rate is only 4.86% at the highest concentration of 100 μg/mL, which is lower than 5% required by Chinese Pharmacopoeia (that is, a hemoglobin release rate caused by nanoparticles entering blood is less than 5%). Therefore, the results of the hemolysis test further prove that MR780 NPs have excellent biocompatibility.

1.3.2 Induction of Macrophage Differentiation

RAW264.7 cells at a logarithmic growth phase were plated in a 6-well plate at a density of $1 \times 10^5$ cells/mL, then a DMEM was added at 2 mL/well, the plate was incubated overnight, and then interleukin-4 (IL-4) was added to the culture at a final concentration of 20 ng/mL. The IL-4 was an M2 macrophage inducer. In a control group, an M1 macrophage inducer lipopolysaccharide (LPS) was added to the culture at a final concentration of 100 ng/mL and then incubated for 24 h.

1.3.3 M2 Macrophage Phenotype Determination

The expression of CD206 on a surface of RAW264.7 cells before and after induction was determined by FCM. Cells were digested and centrifuged, 0.5 μg of mouse CD16/32 monoclonal antibody (mAb) was added, and a resulting mixture was incubated at room temperature for 10 min. Then 0.5 mL of a 1× fixation buffer was added, a resulting mixture was incubated in the dark for 20 min and then centrifuged at 350 g for 5 min, and a resulting supernatant was discarded. 2 mL of a membrane disruption solution was added, and a resulting suspension was centrifuged at 350 g for 5 min; and the operation was repeated once. The cells were resuspended in 100 μL of a membrane disruption solution, 1.25 μL of a PE/cy7 anti-human CD206 antibody was added, and the cells were incubated for 20 min at room temperature in the dark. 2 mL of a membrane disruption solution was added to resuspend cells, a resulting suspension was centrifuged at 350 g for 5 min, and a resulting supernatant was discarded; and the operation was repeated once. 200 μL of PBS was added to resuspend the cells, and the expression of CD206 on a cell surface in each of the two groups was detected by FCM.

Figure 6A:
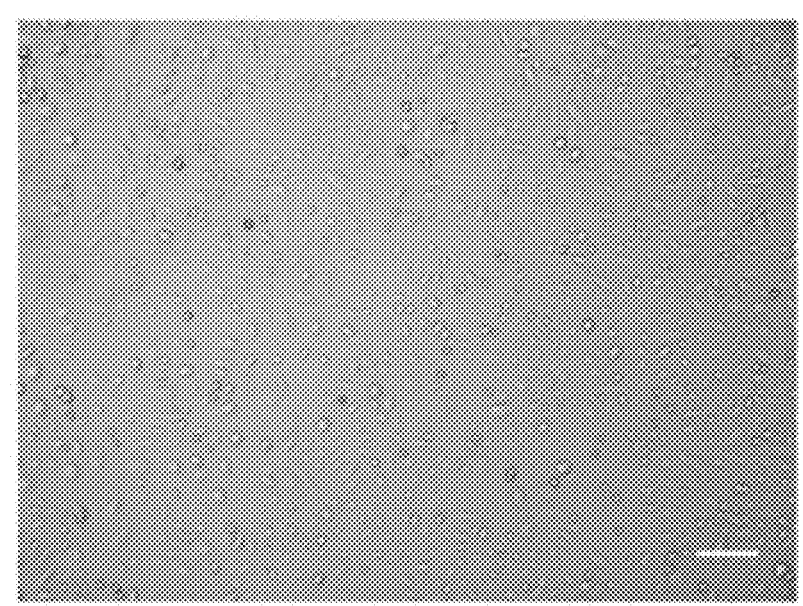
FIG. 6A shows the cell morphology of RAW264.7 cells induced by IL-4 for 24 h (scale bar=100 m)
Figure 6B:
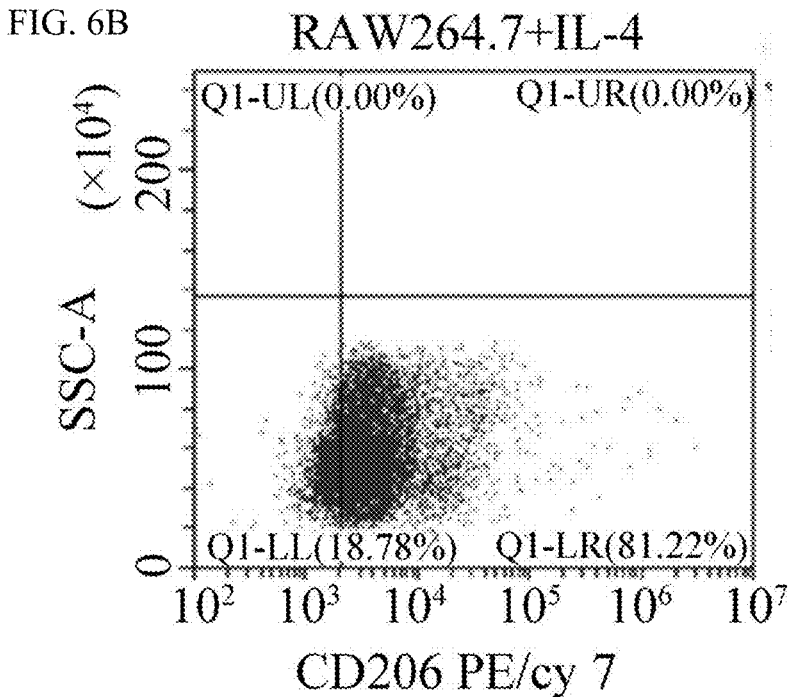
FIG. 6B shows the expression (detected by flow cytometry (FCM)) of PE/cy7-labeled CD206 in RAW264.7 cells incubated with IL-4 for 24 h.
Figures 6C, 7A:
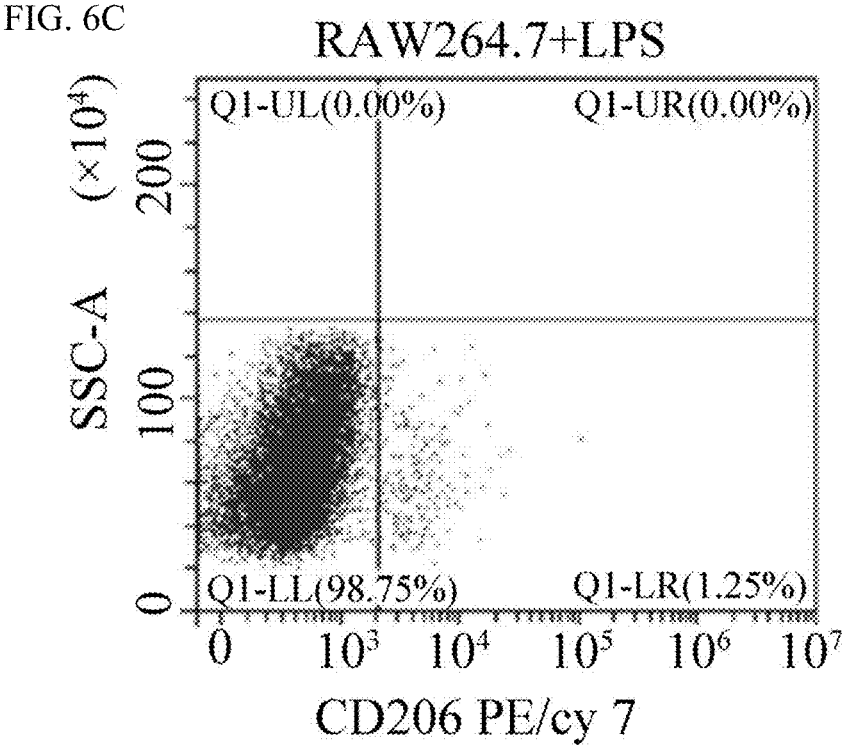
FIG. 6C shows the expression (detected by FCM) of PE/cy7-labeled CD206 in RAW264.7 cells incubated with LPS for 24 h.
FIG. 7A shows the intracellular FITC fluorescence signals detected by FCM after the induced RAW264.7 cells are incubated with 10 μL, 20 μL, 30 μL, 40 μL, and 50 μL of each of 2 mg/mL FITC-MR780 NPs and FITC-DSPC NPs for 2 h

It can be seen from FIG. 6 that, after IL-4 is added to RAW264.7 cells and the cells are cultivated for 24 h, the macrophages have more synapses in morphology (A in FIG. 6); according to FCM assay results of the expression of CD206 on a cell surface in each group labeled by the PE/cy7 anti-human CD206 antibody, after IL-4 is added, the phenotype of RAW264.7 cells is converted into M2, and the expression of CD206 significantly increases to 81.22±0.64% (B in FIG. 6); in the control group, after the M1 macrophage inducer LPS is added to RAW264.7 cells, the expression of CD206 on a cell surface is very low, which is only 1.25±0.23% (C in FIG. 6); and there is a significant statistical difference between the two groups (t=21.21, P<0.05). It can be known that the RAW264.7 cells, after being incubated with IL-4 for 24 h, can be successfully converted into the M2 phenotype.

1.3.4 Targeting Experiment of MR780 NPs on M2 Macrophages 1.3.4.1 Uptake of M2 Macrophages for MR780 NPs Due to the lack of glutathione production in the cell experiment, MR780 NPs cannot undergo an oxidation-reduction reaction to restore fluorescence, and thus the DSPE-FITC fluorescent probe (FITC-MR780 NPs) is self-assembled on a surface of MR780 NPs for tracing, as described above. Induced RAW264.7 cells were incubated in 6-well cell culture plate at a density of $1 \times 10^6$ cells/well. A complete medium DMEM was added, 40 μg/mL FITC-MR780 NPs (experimental group) and 40 μg/mL FITC-DSPC NPs (control group) were each added, and co-incubation was conducted for 1 h, 2 h, 4 h, and 6 h. The induced RAW264.7 cells were incubated with each of FITC-MR780 NPs and FITC-DSPC NPs at concentrations of 20 μg/mL, g/mL, 60 μg/mL, 80 μg/mL, and 100 μg/mL (that is, with 10

μL, 20 μL, 30 μL, 40 μL, and 50 μL of each of 2 mg/mL FITC-MR780 NPs and 2 mg/mL FITC-DSPC NPs) for 2 h, and a fluorescence signal of FITC in cells of each group was determined by FCM. A sample size was $1 \times 10^6$ cells; and a fluorescence intensity in $1 \times 10^4$ cells was randomly determined, and then an average was taken.

Figure 7B:
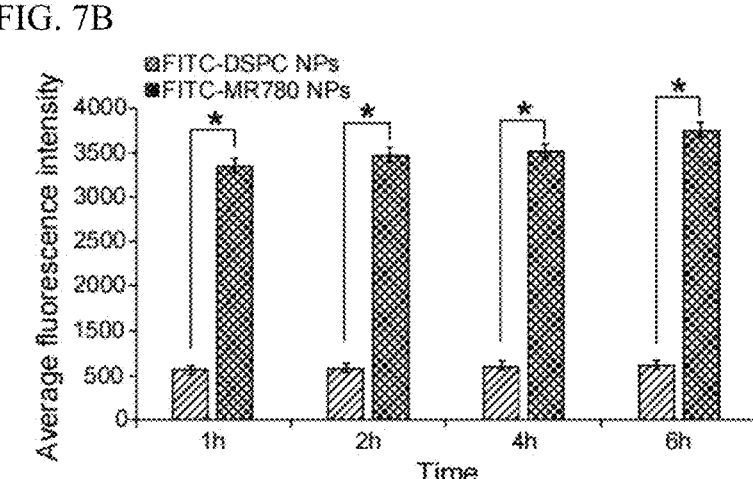
FIG. 7B shows the intracellular FITC fluorescence signals detected by FCM after the induced RAW264.7 cells are incubated with 20 L of FITC-MR780 NPs and 20 μL of FITC-DSPC NPs for 1 h, 2 h, 4 h, and 6 h.

It can be seen from A in FIG. 7 that the uptake of M2 macrophages increases in a dose-dependent manner with the increase of the MR780 NP dose, but the uptake for FITC-DSPC NPs is very small and does not change significantly with the increase of the dose (t=17.62, P<0.05). It can be seen from B in FIG. 7 that, at 1 h, M2 macrophages can internalize FITC-MR780 NPs in large amounts from the beginning, and an intracellular fluorescence intensity increases rapidly and increases over time; M2 macrophages rarely phagocytose common lipid nanoparticles, and a fluorescence signal slightly increases over time; and there is a statistically significant difference in the phagocytosis of macrophages between the two nanoparticles (t=34.92, P<0.05). Therefore, the addition of the mannose targeting group greatly improves the affinity of MR780 NPs (P<0.05), which shows significant dose and time dependence.

1.3.4.2 Blocking Experiment

The induced RAW264.7 cells were incubated in a 6-well cell culture plate, and after the cells grew adherently, free 4-aminophenyl-α-D-mannopyranoside dissolved in DMEM was added at gradient concentrations of 10 mg/mL, 25 mg/mL, 50 mg/mL, 75 mg/mL, 100 mg/mL. After 2 h of co-incubation, the DMEM was changed, FITC-MR780 NPs 40 μg/mL was added in each group, and then co-incubation was conducted for 2 h. A fluorescence signal of FITC in cells of each group was determined by FCM.

Figure 8:
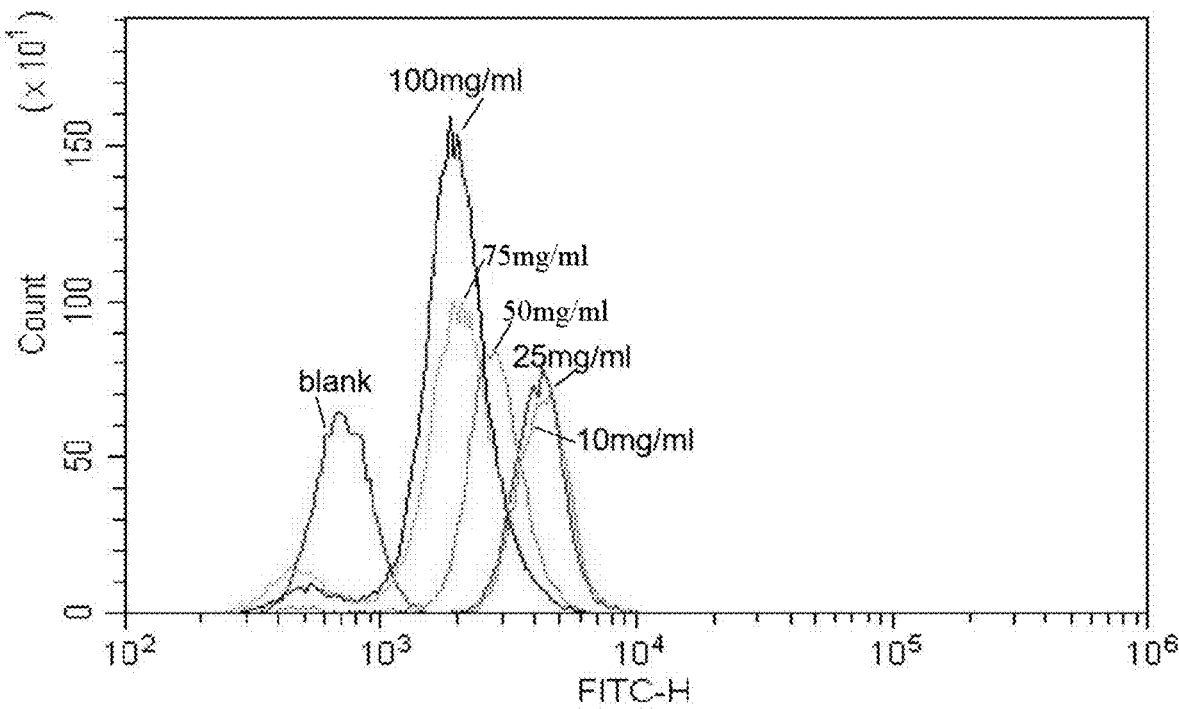
FIG. 8 shows the intracellular FITC fluorescence signals detected by FCM after free mannose is added at different concentrations for pre-blocking and then 20 μl of FITC-MR780 NPs was added to incubate for 2 h.

2 h before the blocking experiment, free mannose was added in advance at different concentrations, then FITC-MR780 NPs were added, and then co-incubation was conducted for 2 h. An intracellular fluorescence intensity of FITC was determined by FCM. As shown in FIG. 8, the phagocytosis of cells for FITC-MR780 NPs decreases significantly with the increase of the free mannose concentration.

The uptake and blocking experiments show that FITC-MR780 NPs and CD206 undergo the specific antigen-antibody binding, which accelerates the specific uptake of M2 macrophages. In conclusion, the mannose group for surface modification of MR780 NPs has a very stable targeting effect on M2 TAMs.

1.3.4.3 Experiments on the Intracellular Distribution of FITC-MR780 NPs and the Biological Behavior of Entering Cells In order to detect the intracellular distribution of FITC-MR780 NPs and the biological behavior of entering cells, the induced RAW264.7 cells were inoculated on a 12 mm glass cover slip and incubated with 40 mg/mL FITC-MR780 NPs for 1 h, 2 h, 4 h, and 6 h. Then a red lysosome fluorescent probe was used to stain at a working solution concentration of 50 nm for 30 min, nuclei were stained with 4',6-diamidino-2-phenylindole (DAPI) for 5 min, and then the glass cover slip was washed three times with PBS for confocal microscopy.

Figure 9:
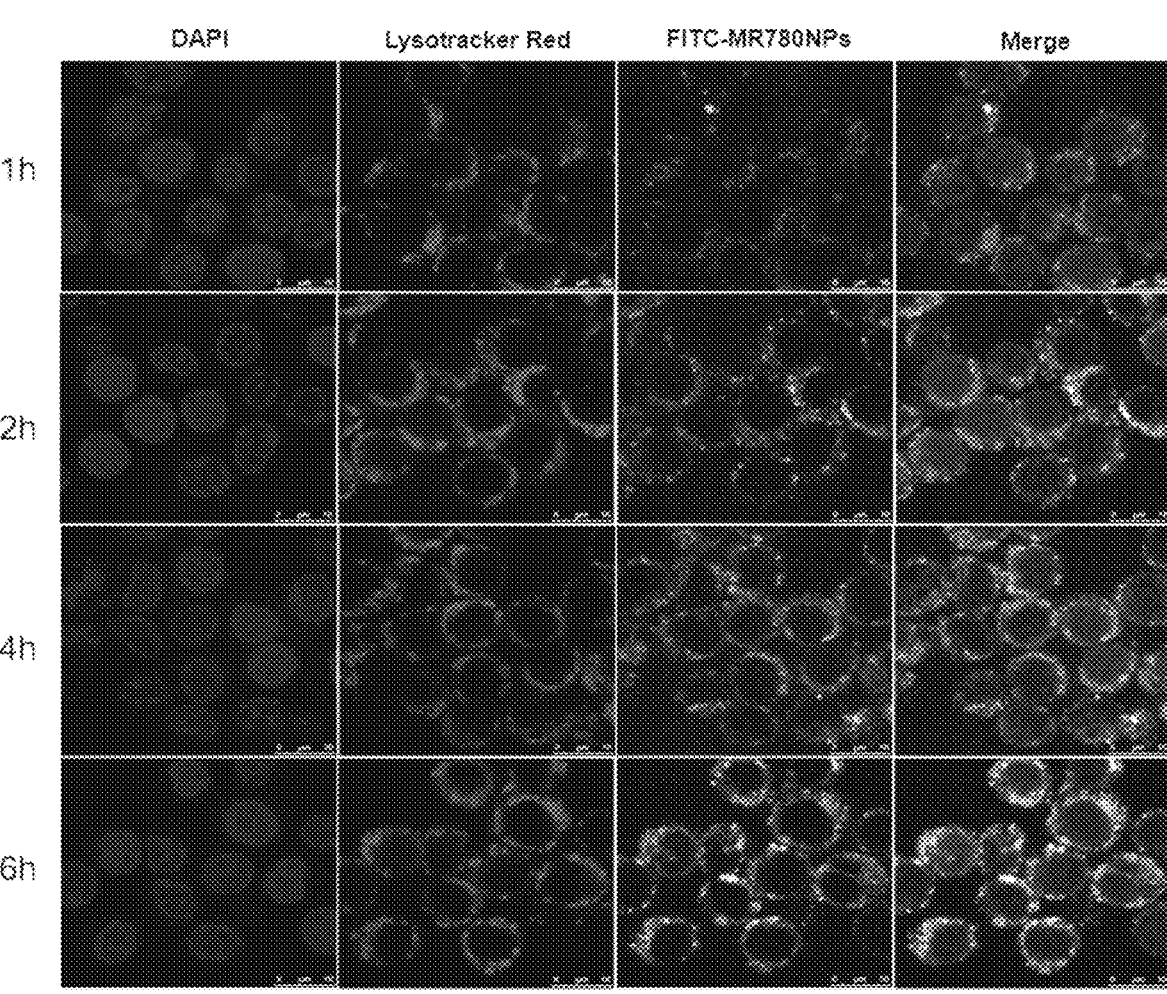
FIG. 9 shows the confocal microscopy images of the phagocytosis of M2 macrophages for FITC-MR780 NPs (scale bar=10 m)
Figure 10A:
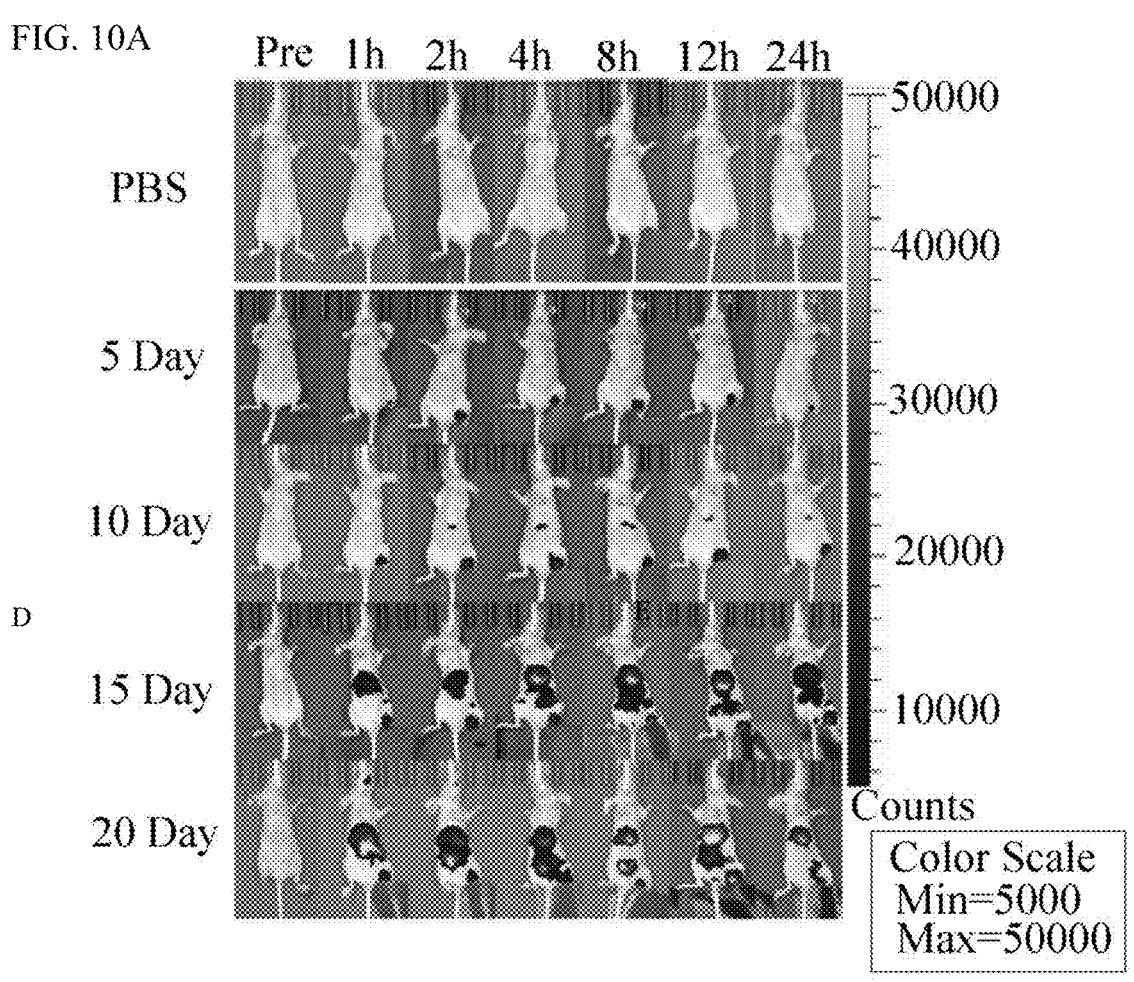
FIG. 10A shows the fluorescence imaging of lymph nodes in control mice plantarly injected with PBS and plantar 4T1 tumor-bearing mice on day 5, day 10, day 15, and day 20.
Figure 10B:
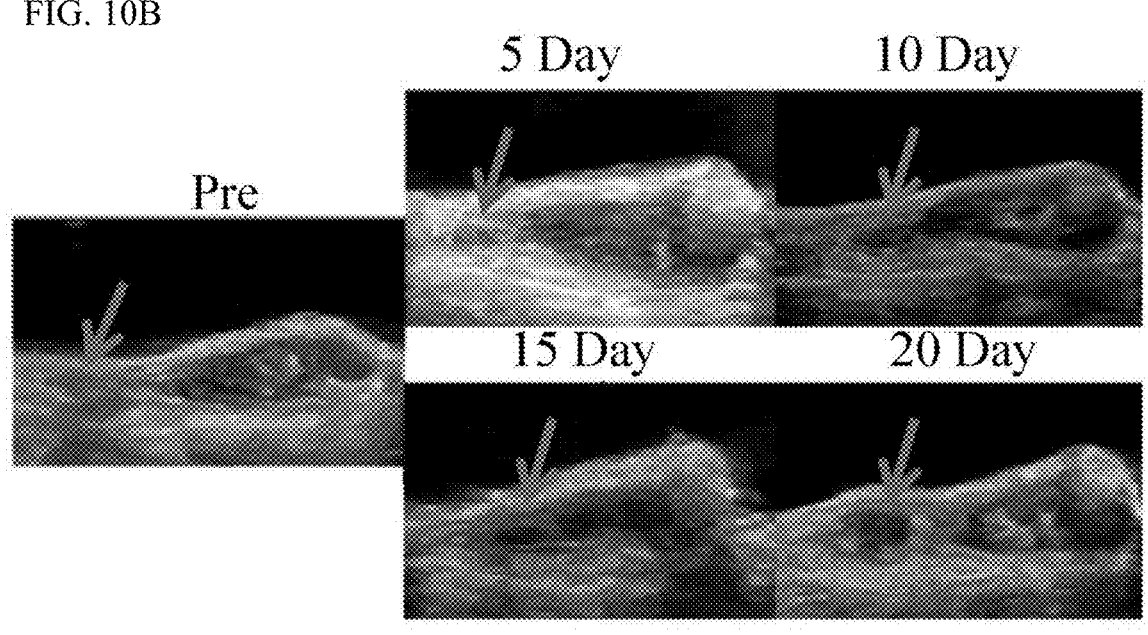
FIG. 10B shows the ultrasound imaging of popliteal lymph nodes in 4T1 tumor-bearing mice on day 0, day 5, day 10, day 15, and day 20 of inoculation (the arrows indicate the popliteal lymph nodes)
Figure 10C:
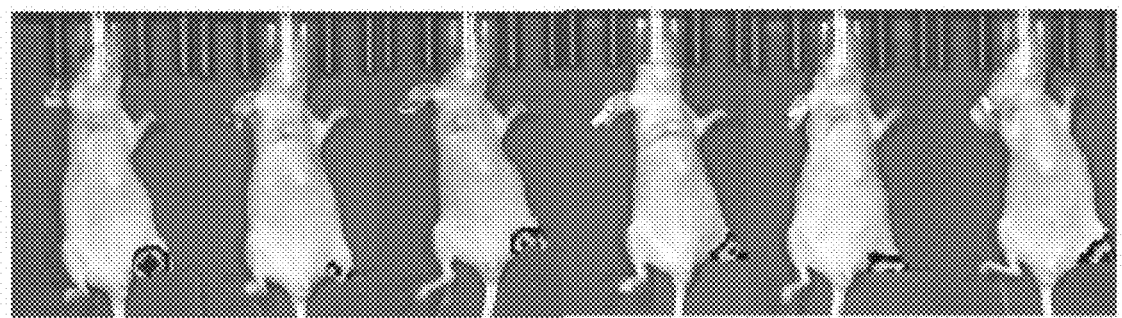
FIG. 10C shows the lymph node bioluminescence in plantar 4T1 tumor-bearing mice on day 5.
Figure 10D:
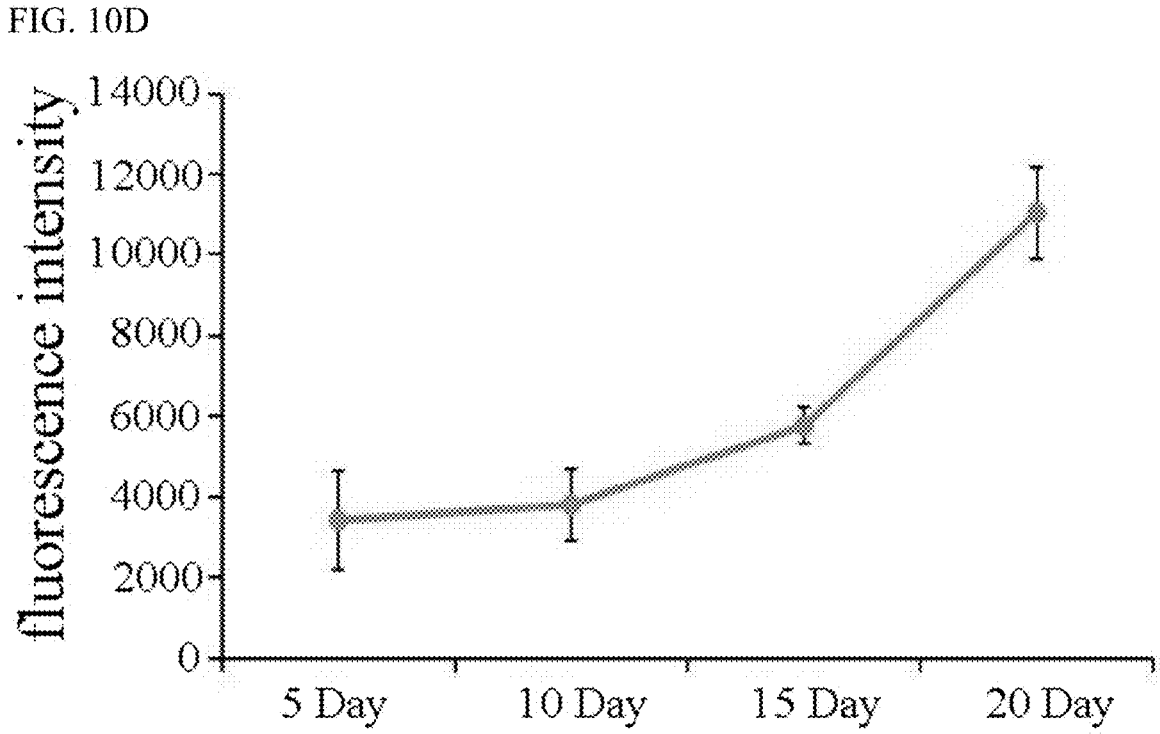
FIG. 10D shows the change of the fluorescence intensity of injected MR780 NPs with tumor progression at 12 h.
Figure 10E:
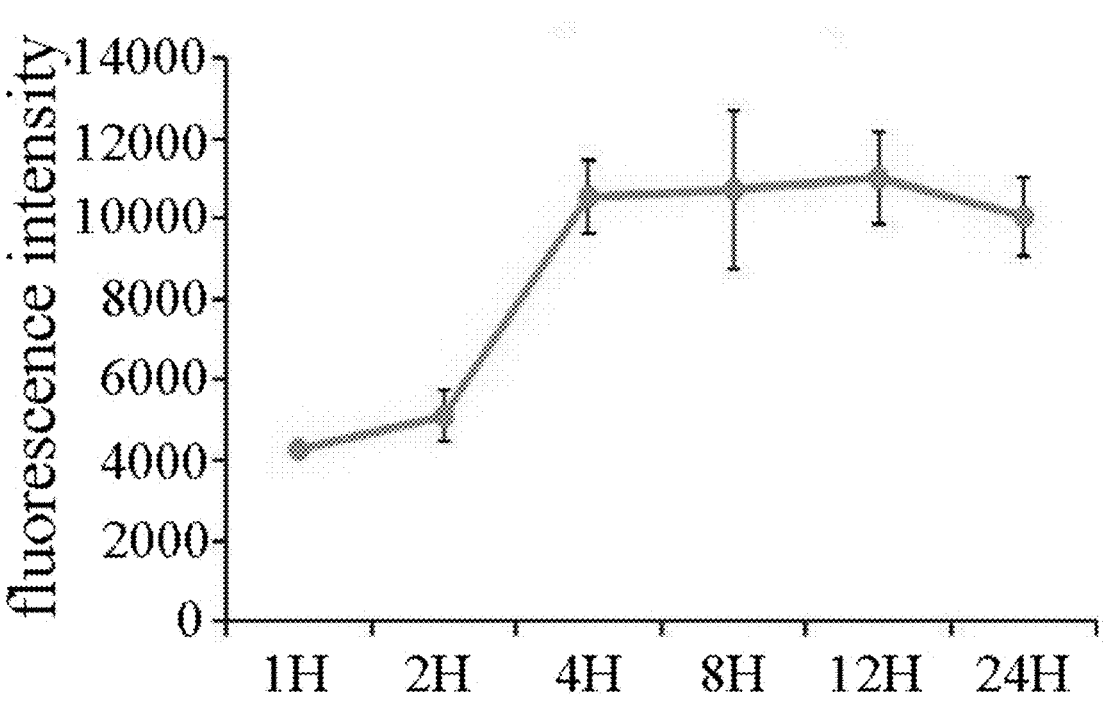
FIG. 10E shows the change of the fluorescence intensity of MR780 NPs at each time point on day 20.
Figure 10F:
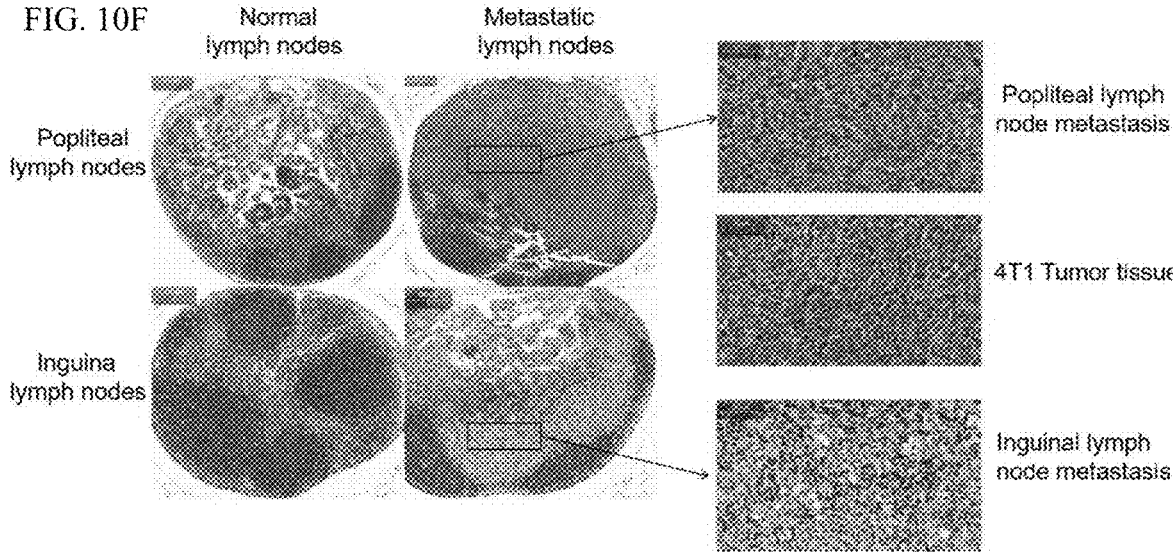
FIG. 10F shows the H&E staining of metastatic lymph nodes (scale bar: 200 mm and 50 mm)
Figure 14:
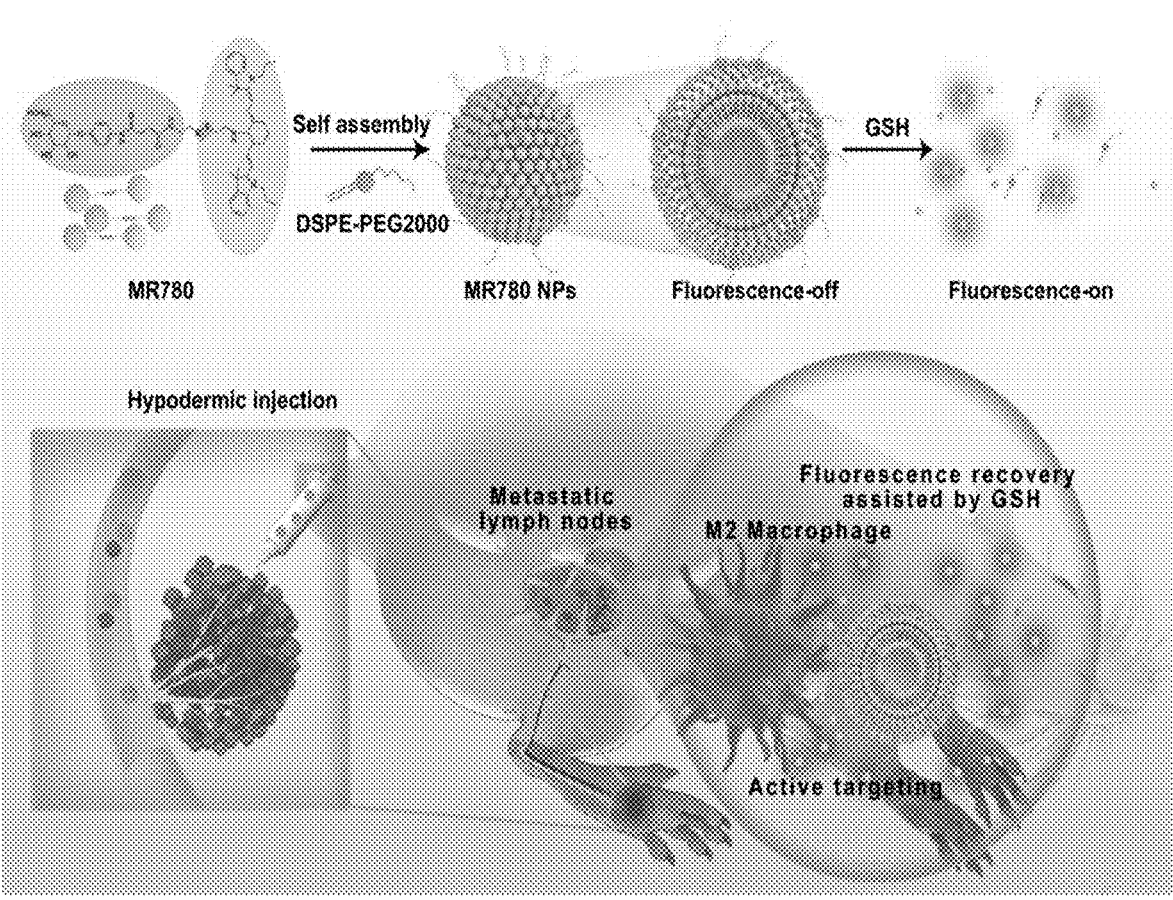
FIG. 14 is a schematic diagram illustrating the preparation and function of MR780 NPs.

It can be seen from FIG. 9 that, according to the confocal microscopy results of the biological behavior of internalization of M2 macrophages for FITC-MR780 NPs, at 1 h of co-incubation, FITC-MR780 NPs begin to enter the cells and are mostly adhered to the cell membrane, which is a critical period for the binding of FITC-MR780NPs to CD206; at 2 h, it is observed that the green fluorescence signal on the cell membrane gradually increases; at 4 h, a large number of nanoparticles enter the cells and are co-localized with the red fluorescence signal of lysosome; and at 6 h, the FITC-MR780NPs are stable in the cells and continuously emit a strong fluorescence signal, which is consistent with the FCM results. The ability of TAMs to phagocytose foreign substances is reduced, but the mannose receptor CD206 on their surface shows a very prominent phagocytosis specificity for FITC-MR780 NPs with a targeting group, which is the advantage of using a targeting preparation to distinguish metastatic lymph nodes from normal lymph nodes.

1.4 Animal Experiment 1.4.1 Establishment of LNM Models

Female 6-week-old Balb/c nude mice were taken and divided into 2 groups, with 10 mice in each group. In an experimental group, LNM models were established, that is, left hind paw pads of female Balb/c mice were each injected with $2 \times 10^5$ 4T1-FLUC cells. In a control group, left hind paw pads of mice were each injected with a same amount of PBS.

1.4.2 Non-Invasive Imaging of Metastatic Lymph Nodes

Sonographic images of lymph nodes in the popliteal fossa of mice were acquired by ultrasound before tumor cell inoculation. To explore the non-invasive detection potential of MR780 NP-targeted imaging for tumor LNM, MR780 NPs (2 mg/kg) were subcutaneously injected into left hind paws of mice in each group on day 5 after the $2 \times 10^5$ 4T1-FLUC cells were inoculated. The IVIS small animal in vivo fluorescence imaging system was used to detect the left hind paws of mice at different time points (0 h, 1 h, 2 h, 4 h, 8 h, 12 h, and 24 h) after injection to obtain fluorescence images of tumor growth and LNM, and then analysis was conducted with the IVIS imaging spectroscopy system under specified parameters (Lex ¼ 640 nm, LEM ¼ 740 nm, color scale min=5000 max=50000). D-fluorescein sodium salt was injected intraperitoneally at 150 mg/kg, and 10 min after the injection, an image of LNM in mice was detected by IVIS bioluminescence and used as a positive standard control, which was compared with the NIR fluorescence image of MR780 NPs. The popliteal lymph nodes in the two groups were then detected every 5 d through ultrasound and fluorescence imaging, and the changes in lymph node images of the two groups were compared.

It can be seen from FIG. 10 that, after MR780 NPs (2 mg/kg) were subcutaneously injected into left hind soles of nude mice in each of the two groups, no significantly-enhanced lymph node fluorescence signal is observed in the PBS control group (A in FIG. 10), but an obvious fluorescence signal is observed in the left popliteal lymph nodes 5 d after tumor bearing in the experimental group. LNM is verified by bioluminescence imaging (C in FIG. 10). Ultrasound results (B in FIG. 10) show that, on day 5 and day 10, there is no significant difference in the sonographic images of lymph nodes between the two groups; and on day 15 to day 20, the popliteal lymph node cortex of tumor-bearing mice is thickened, but it is difficult to determine whether there is LNM by ultrasound. From day 15, in addition to the popliteal lymph nodes, fluorescence images of the left inguinal lymph nodes were also detected by the in vivo fluorescence imaging (A in FIG. 10); and the fluorescence signal continues to increase with the tumor progression (D in FIG. 10), which reaches a high level at 4 h of injection and begins to decline at 12 h (E in FIG. 10). Pathological results further confirm that the detected lymph nodes do undergo metastasis (F in FIG. 10).

Non-invasive imaging results show that MR780 NPs have high specificity and show a significant fluorescence signal only in metastatic lymph nodes. On day 5 of tumor bearing, a lymph node signal is detected by fluorescence imaging after peritumoral injection of MR780 NPs (A in FIG. 10), and at this time point, a minor diameter of the lymph nodes is only 2 mm as detected by ultrasound and there is no obvious change in the morphological structure (F in FIG. 10), which means that MR780 NPs can capture a significant fluorescence signal of micrometastasis when the metastatic lymph nodes are only 2 mm in the minor diameter. This provides a valuable support for treatment selection. On day 15, in addition to the popliteal lymph nodes, sonographic images of left inguinal lymph nodes are detected by the in vivo fluorescence imaging, indicating that the tumor cells further spread and metastasize to distant sites. On day 20, the fluorescence signal is further enhanced (C and D in FIG. 10). The sensitivity of MR780 NPs is beneficial for the diagnosis of distant metastasis. In metastatic lymph nodes, the mannose on a surface of MR780 NPs tightly binds to the mannose receptor CD206 on a surface of TAMs, and thus the drug continuously accumulates in metastatic lymph nodes. There is a large amount of reduced glutathione in a tumor microenvironment, and the reduced glutathione can react with the disulfide bond in MR780 NPs, such that the disulfide bond is broken, the fluorescence signal of MR780 NPs blocked in advance is restored, and a significant fluorescence signal of metastatic lymph nodes can be detected in IVIS. However, in normal lymph nodes, MR780 NPs cannot be deposited in large amounts in the lymph nodes due to the lack of expression of the CD206 receptor on TAMs, and there is a lack of reduced glutathione in normal lymph nodes, such that the disulfide bond cannot be broken and the fluorescence signal of MR780 NPs cannot be restored. Therefore, metastatic lymph nodes can be accurately distinguished from normal lymph nodes.

1.4.3 Resection of Metastatic Lymph Nodes Under Fluorescence Navigation 20 d after the inoculation, MR780 NPs were injected, and 24 h later, the final fluorescence imaging and ultrasound imaging were completed. The skin of mice was removed to expose the lymph nodes, and the fluorescence imaging was conducted with an IVIS imaging spectroscopy system (1ex ¼ 640 nm, 1em ¼ 740 nm, color scale min=20000 max=50000). Under fluorescence navigation, the lymph nodes with the fluorescence signal of MR780 NPs were resected. The in vivo imaging was then repeated to confirm that the resected lymph nodes had the fluorescence signal. The vital organs such as heart, liver, spleen, lung, kidneys, and lymph nodes were dissected for fluorescence imaging, and the tissue distributions of the contrast agent MR780 NPs in mice of the two groups were compared. To further confirm tumor LNM, mice were euthanized on day 1, day 10, and day 20 after injection of MR780 NPs, and lymph nodes, tumors, and other major organs surgically resected were fixed with 4% paraformaldehyde. The tissue was then embedded in paraffin, and histopathological analysis was conducted with hematoxylin-eosin.

As shown in FIG. 11, in the experimental group, in addition to the tumor in situ fluorescence signal and the popliteal and inguinal lymph nodes detected preoperatively, distant ipsilateral axillary lymph nodes were also detected after exposure (A in FIG. 11). With the help of fluorescence navigation, metastatic lymph nodes were resected, and then fluorescence detection was conducted once again. Detection results showed that the resected lymph nodes had the fluorescence signal of MR780 NPs (B in FIG. 11). The heart, liver, spleen, lung, kidneys, and lymph nodes were then taken out for in vitro fluorescence imaging (C in FIG. 11).

Multiple metastatic lymph node signals were found in the tumor-bearing group, while no significant fluorescence signal was found in lymph nodes of the normal group. The lymph node uptake was normalized to the tumor fluorescence intensity through a dose of the injected probe, and there was a significant difference between the two groups (P<0.05).

As shown in FIG. 12, compared with the normal group, the tissue morphology was still normal after injection of MR780 NPs (p>0.05).

In conclusion, in the experimental group, although the size of metastatic lymph nodes is small, the fluorescence signal is very strong, which further reflects that the MR780 NPs have strong targetability and the metastatic lymph nodes can be accurately and safely resected under fluorescence navigation.

1.4.4 Immunofluorescence Staining

The lymph nodes of normal mice and the metastatic lymph nodes resected under fluorescence navigation were subjected to immunofluorescence staining, and staining results were analyzed. For CD206 analysis, frozen sections were incubated with a rabbit anti-mouse CD206 antibody and then visualized with an F488-conjugated secondary antibody under a confocal microscope. For KI67 analysis, frozen sections were incubated with a rat anti-mouse KI67 antibody and then visualized with a Cy-3-conjugated secondary antibody.

The lymph nodes resected under fluorescence navigation in the experimental group and the control group were subjected to immunohistochemical pathological analysis, and K167 was used to evaluate the proliferation ability of tumor cells in the lymph nodes. It can be seen that the staining of KI67 in the metastatic lymph nodes is significantly higher than that in the normal lymph nodes (p<0.05), indicating that the tumor cells are in a high proliferation state in the lymph nodes and there is tumor metastasis (A in FIG. 13). The CD206 staining of lymph nodes shows that a content of CD206 in the metastatic lymph nodes is significantly higher than that in the normal group (p<0.05), and there is the co-localization phenomenon that is very consistent with the red signal of MR780 NPs (B in FIG. 13), which further reflects the specific antigen-antibody binding of MR780 NPs to CD206 on a surface of TAMs in the tumor microenvironment.

The present disclosure discovers for the first time that a large number of M2 TAMs are recruited in a tumor microenvironment of metastatic lymph nodes of breast cancer, and thus MR780 NPs can specifically bind to CD206 on a surface of TAMs. MR780 NPs accumulate in lymph nodes invaded by tumor cells and undergo an oxidation-reduction reaction with reduced glutathione in a tumor microenvironment, which triggers a fluorescence signal of MR780 NPs; and MR780 NPs do not accumulate and do not show fluorescence in normal lymph nodes. Therefore, the fluorescent contrast agent of the present disclosure can be used to diagnose LNM of breast cancer, realize the preoperative evaluation of LNM, assist in the clinical determination of tumor staging and the formulation of a surgical plan, and achieve the accurate resection under intraoperative fluorescence navigation. The fluorescent contrast agent of the present disclosure has the characteristics of strong specificity and high sensitivity, and is expected to be a new method used in the clinical diagnosis and resection of metastatic lymph nodes.

The above descriptions are merely preferred implementations of the present disclosure. It should be noted that a person of ordinary skill in the art may further make several improvements and modifications without departing from the principle of the present disclosure, but such improvements and modifications should be deemed as falling within the protection scope of the present disclosure.

What is claimed is:

1. A fluorescent contrast agent with a targeting function, wherein the fluorescent contrast agent comprises a targeting material, a fluorescent probe, and a nanoformulation material; and in the fluorescent contrast agent, the nanoformulation material serves as a carrier, wherein the targeting material and the fluorescent probe are linked to each other through a disulfide bond molecule;

wherein the nanoformulation material is PEGylated phospholipid;

wherein the targeting material is mannose and/or a mannose derivative.

2. The fluorescent contrast agent according to claim 1, wherein the fluorescent contrast agent has a particle size of 65 nm to 80 nm.

3. The fluorescent contrast agent according to claim 1, wherein the fluorescent probe is IR780, Cy5.5, IR820, Cy7, or Cy7.5.

4. The fluorescent contrast agent according to claim 1, wherein a disulfide bond molecule-containing compound comprises one selected from the group consisting of cystamine, 3-[(3-amino-3-oxopropyl)dithio]propanamide, and D-cystine.

5. The fluorescent contrast agent according to claim 1, wherein the mannose derivative comprises 4-aminophenyl-α-D-mannopyranoside or D-mannosamine hydrochloride.

6. The fluorescent contrast agent according to claim 1, wherein the PEGylated phospholipid comprises DSPE-PEG2000, DSPE-PEG5000, DPPE-PEG2000, DPPE-PEG5000, DMPE-PEG2000, or DMPE-PEG5000.

7. A preparation method of the fluorescent contrast agent according to claim 1, comprising the following steps:

subjecting mannose or a mannose derivative to a carboxylation reaction with succinic anhydride to obtain carboxylated mannose or a carboxylated mannose derivative;

subjecting the fluorescent probe to an amination reaction with a disulfide bond molecule-containing compound to obtain an amino-modified fluorescent probe;

activating the carboxylated mannose or carboxylated mannose derivative, and subjecting the activated carboxylated mannose or carboxylated mannose derivative to a condensation reaction with the amino-modified fluorescent probe to obtain a mannose/mannose derivative-fluorescent probe conjugate; and subjecting the mannose/mannose derivative-fluorescent probe conjugate, PEGylated phospholipid, and water to ultrasonic dispersion to obtain the fluorescent contrast agent.

8. The preparation method according to claim 7, wherein the carboxylated mannose or carboxylated mannose derivative is activated with a 1-ethyl-3-(3-dimethylaminopropyl) carbodiimide salt.

9. The preparation method according to claim 7, wherein a molar ratio of the carboxylated mannose or carboxylated mannose derivative to the succinic anhydride is 1:(2-10).

10. The preparation method according to claim 7, wherein a molar ratio of the carboxylated mannose or carboxylated mannose derivative to the amino-modified fluorescent probe is (1-10):1.

11. The preparation method according to claim 7, wherein the ultrasonic dispersion is conducted for 5 min to 30 min with an ultrasonic temperature of 20° C. to 60° C. and an ultrasonic power of 50 W to 500 w.

12. The preparation method according to claim 7, wherein the carboxylation reaction and the amination reaction are each conducted in an organic solvent.

13. The preparation method according to claim 7, wherein the amination reaction between the fluorescent probe and the disulfide bond molecule-containing compound is conducted in the presence of a catalyst.

14. The preparation method according to claim 12, wherein the organic solvent comprises N,N-dimethylformamide (DMF), N,N-dimethylacetamide (DMA), or dimethyl sulfoxide (DMSO).

15. The preparation method according to claim 13, wherein the catalyst comprises 2,6-diisopropylaniline (DIPA), triethylamine (TEA), pyridine, N,N-diisopropylethylamine (DIPEA), or 4-dimethylaminopyridine (DMAP).

16. The preparation method according to claim 13, wherein the fluorescent probe, the disulfide bond molecule-containing compound, and the catalyst are in a molar ratio of 1:(5-15):(10-30).

17. A method for targeting M2 tumor-associated macrophages (TAMs), comprising applying the fluorescent contrast agent according to claim 1 to a subject in need.

*    *    *    *    *